United States Patent [19]

Matsumura

[11] Patent Number: 5,066,117
[45] Date of Patent: Nov. 19, 1991

[54] PERIMETER

[75] Inventor: Isao Matsumura, Yokosuka, Japan

[73] Assignee: Canon Kabushiki Kaisha, Tokyo, Japan

[21] Appl. No.: 550,201

[22] Filed: Jul. 10, 1990

Related U.S. Application Data

[63] Continuation of Ser. No. 333,884, Apr. 4, 1989, abandoned, which is a continuation of Ser. No. 191,734, May 2, 1988, abandoned, which is a continuation of Ser. No. 831,703, Feb. 21, 1986, abandoned.

[30] Foreign Application Priority Data

| Feb. 26, 1985 | [JP] | Japan | 60-36781 |
| Feb. 26, 1985 | [JP] | Japan | 60-36782 |
| Mar. 12, 1985 | [JP] | Japan | 60-48629 |
| Mar. 12, 1985 | [JP] | Japan | 60-48630 |
| Mar. 12, 1985 | [JP] | Japan | 60-48631 |

[51] Int. Cl.$^5$ .............................................. A61B 3/02
[52] U.S. Cl. ................................. 351/226; 351/211; 351/224
[58] Field of Search ............... 351/224, 226, 205, 206, 351/211

[56] References Cited

U.S. PATENT DOCUMENTS 4,260,227 4/1981 Munnerlyn et al. ................. 351/226
4,279,478 7/1981 Matsumura .......................... 351/224

Primary Examiner—Paul M. Dzierzynski
Attorney, Agent, or Firm—Fitzpatrick, Cella, Harper & Scinto

[57] ABSTRACT

A perimeter has a predetermined index to be projected onto a fundus of an eye to be examined and an index projection imaging optical system which can form an intermediate image of the index in front of the eye. An optical system as being at least a part of the index-projection imaging optical system, is movable to displace the position of the index image on the fundus of the eye. The index-projection imaging optical system has an image forming section which moves the intermediate image in the direction of the optical axis.

31 Claims, 8 Drawing Sheets

PERIMETER

This application is a continuation of application Ser. No. 333,884 filed Apr. 4, 1989, now abandoned, which is a continuation of application Ser. No. 191,734 filed May 2, 1988, now abandoned, which is a continuation of application Ser. No. 831,703 filed Feb. 21, 1986, now abandoned.

BACKGROUND OF THE INVENTION

1. Field of the Invention

The present invention relates to a perimeter for examining the visual field of an eye of a client to be examined in an ophthalmic hospital or in an optometrist's office.

2. Related Background Art

A visual field means a range of vision when an eye is directed in a predetermined direction. An examination of visual field is very important not only for diagnosing diseases of the eye but also when looking for symptoms of a wide variety of diseases, such as one causing intracranial abnormalities. Conventionally, an apparatus for examining a visual field (i.e., a perimeter) displays a semi-spherical dome in front of the eye to be examined, and an index is projected on the dome. The client then makes subjective judgements about the index, thus performing self-measurement of the visual field. If the client's eye shows anomalous refraction, a diopter correction lens corresponding to a certain refracting power is inserted in a lens frame arranged in front of the eye. However, it is difficult to find a lens perfectly suited for an eye being examined and to accurately examine the visual field because of distortion in index image light near the lens, eclipse of the index image light by a lens frame, an out-of-focus state of the index image light from the lens, and the like.

In the conventional apparatus, a client under examination observes the index in the semi-spherical dome with one eye per each time. In this case, however, since visual field measurement must be performed while shielding the eye not under examination with an eye-shielding member (e.g., an eye-mask), changing the eye-shielding member from side-to-side is cumbersome, and the client is subjected to the examination in an unnatural state, i.e., with one eye closed.

SUMMARY OF THE INVENTION

It is an object of the present invention to provide a perimeter which furnishes a clearly recognizable index image and, more specifically, furnishes a fixed index image without using special-purpose spectacles or diopter correction lenses, and can continuously examine a visual field with an accurate diopter while keeping a correct positional relationship.

It is another object of the present invention to provide a perimeter which can omit cumbersome replacement of an eye-shielding member and which allows a client to be examined in a natural state, i.e., while both his eyes are open.

A perimeter according to the present invention comprises a predetermined index to be projected onto a fundus of an eye to be examined; and an index projection imaging optical system which can form an intermediate image of said index in front of said eye, wherein an optical system as being at least a part of said index projection imaging optical system, is movable to displace a position of the index image on the fundus of said eye, and said index projection imaging optical system comprises image forming means which moves said intermediate image in the direction of the optical axis.

DESCRIPTION OF THE PREFERRED EMBODIMENTS

Figure 1:
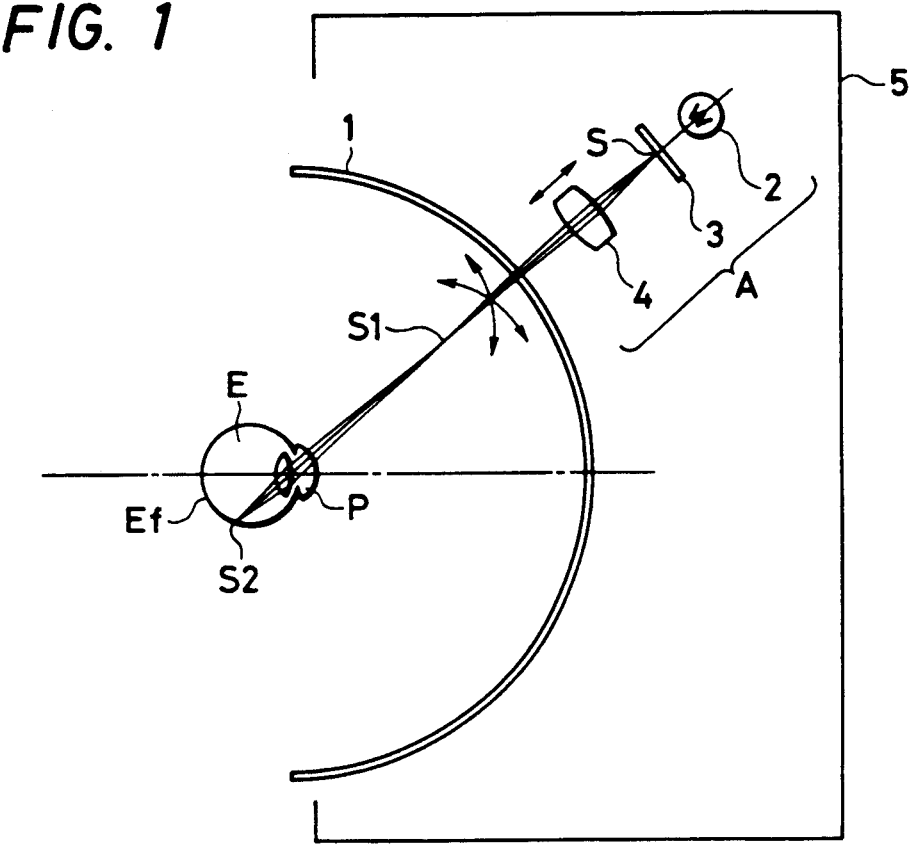
FIGS. 1 to 4 are illustrations showing optical arrangements according to an embodiment of the present invention.

FIG. 1 shows a first embodiment of the present invention. A semi-spherical dome 1, comprising a semi-transparent member having a spherical surface substantially about an iris P of an eye E to be examined, is arranged in front of the eye E. An index optical system A comprising an illumination light source 2, an index plate 3, and a focusing lens 4 is arranged behind the semi-spherical dome 1, and a light-shielding cover 5 is further arranged therebehind so as to shield external light. An index light beam emitted from an index S on the index plate 3 illuminated with the light source 2 is focused by the focusing lens 4 to temporarily form a spatial image S1 (a real or virtual image) in front of the eye E. The beam is guided into the eye E and forms an index image S2 on a fundus Ef thereof. Note that, depending on the position of the focusing lens 4, the beam becomes an afocal beam which does not form the spatial image S1. Furthermore, the optical system A is rotatable three-dimensionally about the iris P of the eye E in order to examine its visual field.

Since the semi-spherical dome 1 is arranged between the eye E and the focusing lens 4, the eye E can only see the index S. A projected position of the index S is shifted in the direction of the optical axis depending on a diopter of the eye E.

Figure 2:
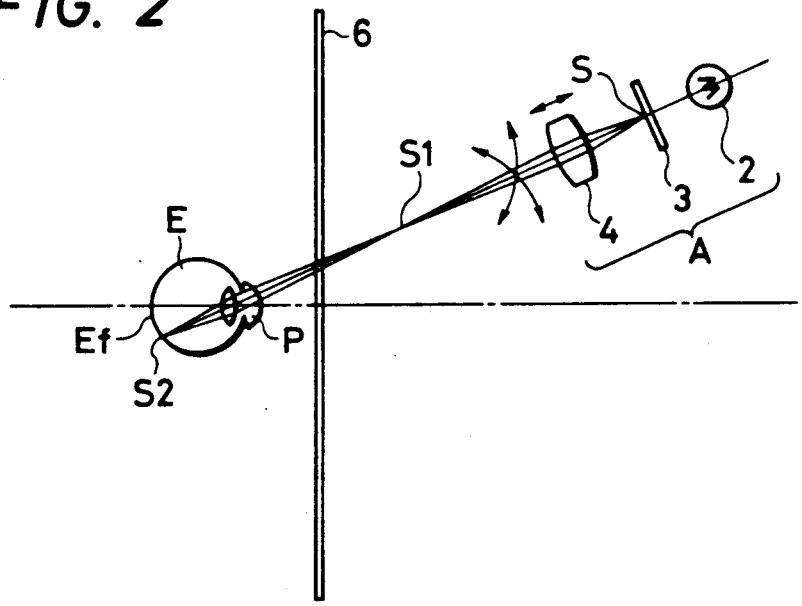

In the above embodiment, the semi-spherical dome 1 is used as a non-diffusing barrier filter. However, the same effect of the present invention can be obtained if a planar screen 6 made of a semi-transparent member is used instead of the dome 1, as shown in FIG. 2. In FIG. 2 and thereafter, the light-shielding cover 5 is omitted for the sake of simplicity.

Figure 3:
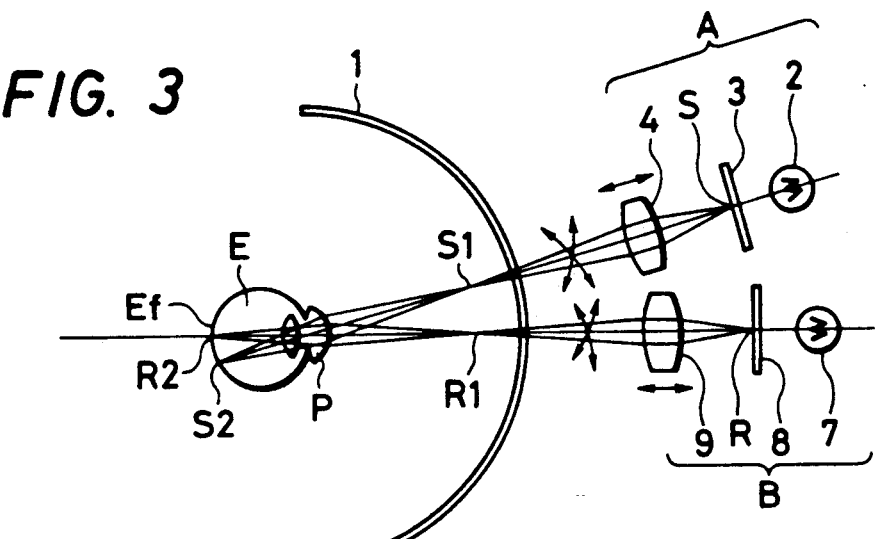

FIG. 3 shows a perimeter according to another embodiment of the present invention. In this embodiment, a fixed index optical system B is provided in addition to the index optical system A shown in FIG. 1. The optical system B comprises an illumination light source 7, a fixed index plate 8 having a fixed index R, and a focusing lens 9. An image beam through the fixed index R illuminated with the light source 7 is temporarily focused by the focusing lens 9 to form a spatial image R1, and is then guided into an eye E so as to form a fixed index image R2, with a fundus Ef as the center thereof.

In the fixed index R, a focusing operation can be performed by moving the focusing lens 9, depending on refracting power of the eye E. In order to actually measure a visual field, the optical system A is rotated about the iris P as in the embodiment of FIG. 1, while fixing the eye E on the fixed index R. Note that the optical system B can be deviated so as to guide the eye E in a different direction from, or not to collide with, the optical system A.

Figure 4:
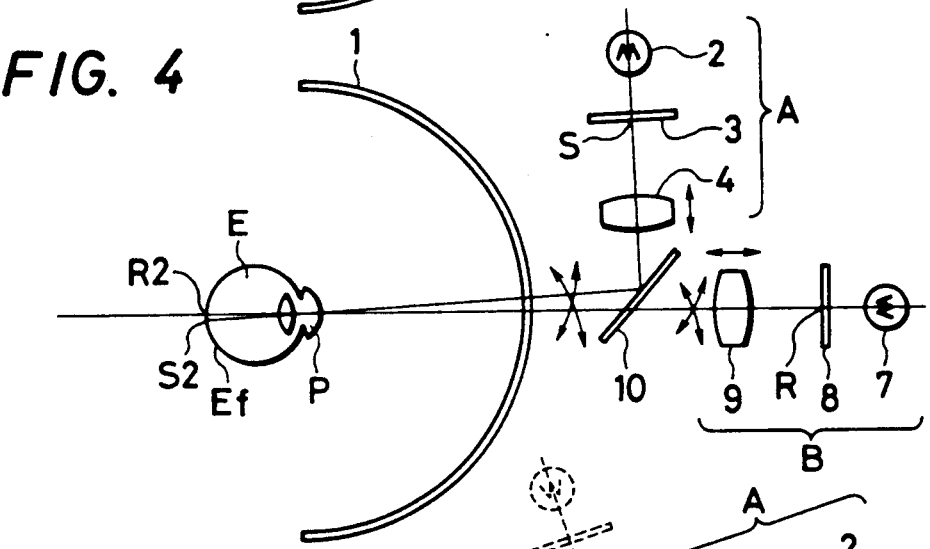

FIG. 4 shows a perimeter according to another embodiment of the present invention. Optical systems A and B of this embodiment are coupled through a beam splitter 10, and an index S is operated near a fixed index R. With this arrangement, a region where the optical systems A and B interfere with each other as in the embodiment shown in FIG. 3 can be removed. Note that the same reference numerals in FIG. 4 denote the same parts as in FIGS. 1 and 3. In this case, the optical system A is arranged to be freely rotatable three-dimensionally about an iris P of an eye E.

Figure 5:
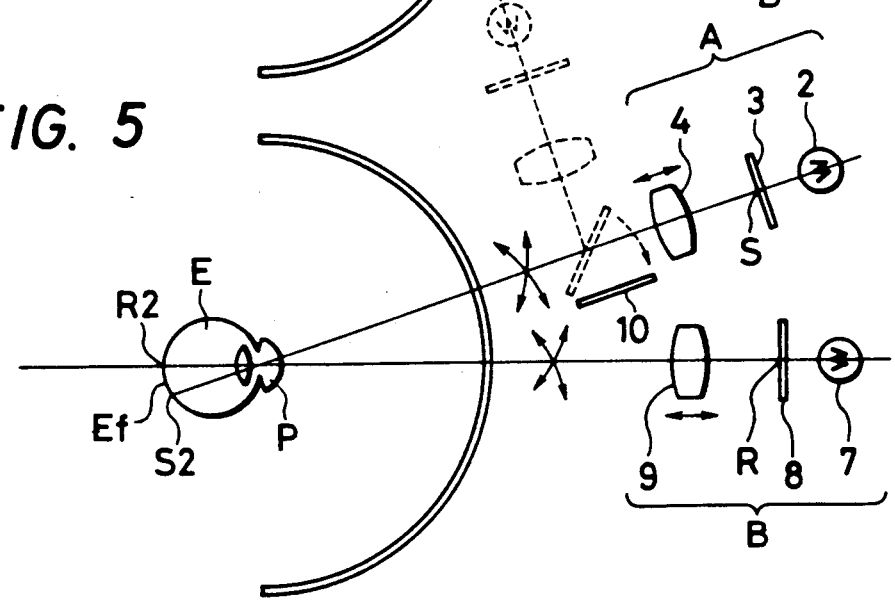
FIG. 5 is an illustration for explaining an operation of the optical arrangement in the embodiment shown in FIG. 4.

In FIG. 4, the fixed index R on the fixed index plate 8 is illuminated with the light source 7, and light therefrom passes through the semi-spherical dome 1 via the focusing lens 9 and the beam splitter 10, then temporarily forming a spatial image. Thereafter, the beam forms a fixed index image R2 with a fundus Ef of the eye E as its center. An index light beam emitted from the index S illuminated with the light source 2 is reflected by the beam splitter 10 through the focusing lens 4, and passes through the semi-spherical dome 1, thus temporarily forming a spatial image. Thereafter, the beam enters the eye E and forms the index image S2 on the fundus Ef. When the index S is operated separately from the fixed index R, the beam splitter 10 pivots from a position indicated by a broken line to a position indicated by a solid line in FIG. 5, and the optical axis including the light source 2, the index plate 3 and the focusing lens 4 of the optical system. A directs the beam linearly toward iris P of the eye E.

It should be noted that the optical system A can be rotated about the optical axis of the focusing lens 9 toward the center of the iris P so as to prevent interference with the optical system B.

In the above embodiment, the index and the fixed index can be arranged to be replaceable or can comprise a liquid crystal material so as to be freely deformed. A filter means for providing various color indexes can be added. Furthermore, a plurality of index optical systems can be provided to perform index conversion alternatively or to synchronize the index optical system with the fixed index system. For the focusing lens, a known special-purpose lens which varies its refracting power by moving a lens in a direction perpendicular to the optical axis can be used, or refracting power can be varied by applying electricity, heat, pressure, and the like to a polymer (e.g., silicone) soft lens.

Figure 6:
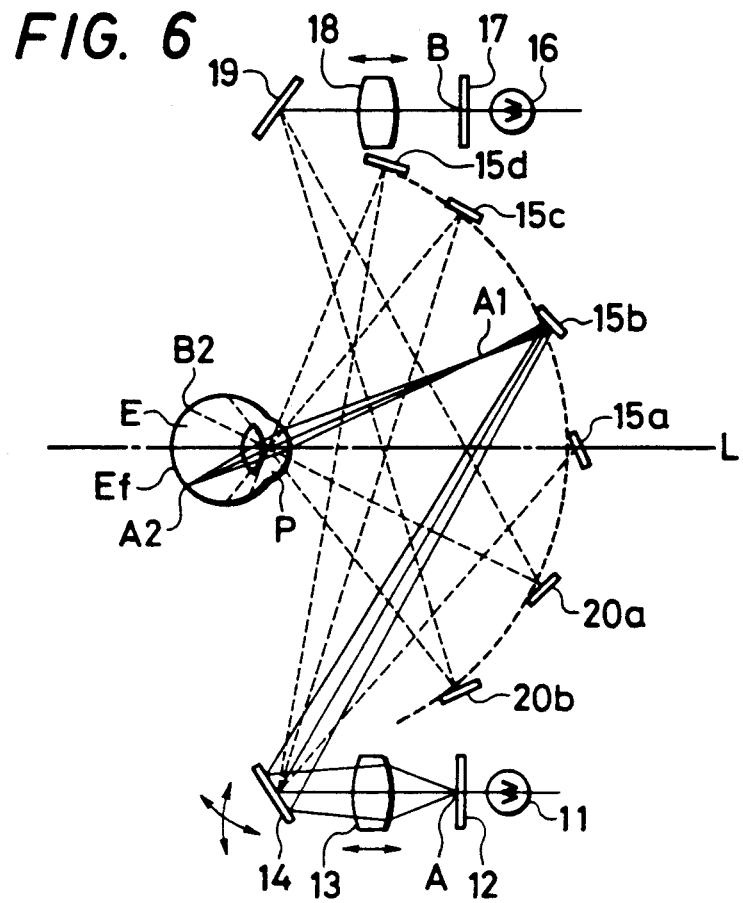
FIG. 6 is an illustration showing an optical arrangement according to another embodiment of the present invention.

FIG. 6 shows a perimeter according to another embodiment of the present invention. A first index-projection imaging optical system is constituted by a lower light source 11, an index plate 12, a focusing lens 13, and a movable mirror 14. A plurality of stationary mirrors 15a, 15b, 15c, 15d, . . . as mirror reflection members are fixed in position above a fixed index axis L, in a semi-spherical dome shape substantially about an eye E to be examined. In FIG. 6, a light beam from an index A on the index plate 12, illuminated with the light source 11, forms a spatial image A1 through the focusing lens 13, the movable mirror 14, and the stationary mirror 15b, and thereafter projects an index image A2 onto a fundus Ef through an iris P of the eye E.

Figure 7:
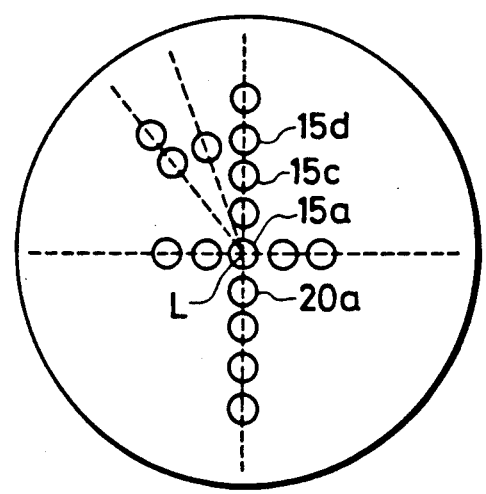
FIG. 7 is an illustration for explaining an arrangement of a stationary mirror.

The focusing lens 13 changes its refracting power or position depending on a diopter of the eye E, so as to form a focal point on the fundus Ef of the eye E, thereby correctly projecting the index image A2 thereon. When the movable mirror 14 is rotated freely, the light beam from the index A can be directed toward the desired stationary mirror 15a, through 15d thereby changing an incident direction of the index image A2 onto the fundus Ef of the eye E. In the stationary mirrors 15a through 15d, as shown in FIG. 7, the respective stationary mirrors 15b, 15c, . . . are regularly arranged with reference to the stationary mirror arranged on the axis L of the eye E in three dimensions, thus providing a predetermined field angle for the index image A2.

A second index-projection imaging optical system is arranged symmetrically with the first optical system about the axis L. An image based on an index B on an index plate 17 illuminated with an upper light source 16 is guided into the eye E through a focusing lens 18, a movable mirror 19, and a plurality of stationary mirrors 20a, 20b, . . . arranged below the axis L in a semi-spherical dome shape, thus forming an index image B2 on the fundus Ef of the eye E. The focusing lens 18 changes its refracting power or its position depending on the diopter of the eye E, as does the focusing lens 13, and the stationary mirrors 20a, 20b perform the same function as the mirrors 15a through 15d.

In the above embodiment, the first and second index-projection imaging optical systems directed by the stationary mirrors 15a–15d and 20a–20b are provided, and are used separately, depending on the positions of the mirrors 15a–15d and 20a–20b. However, they can also be combined.

Figure 8:
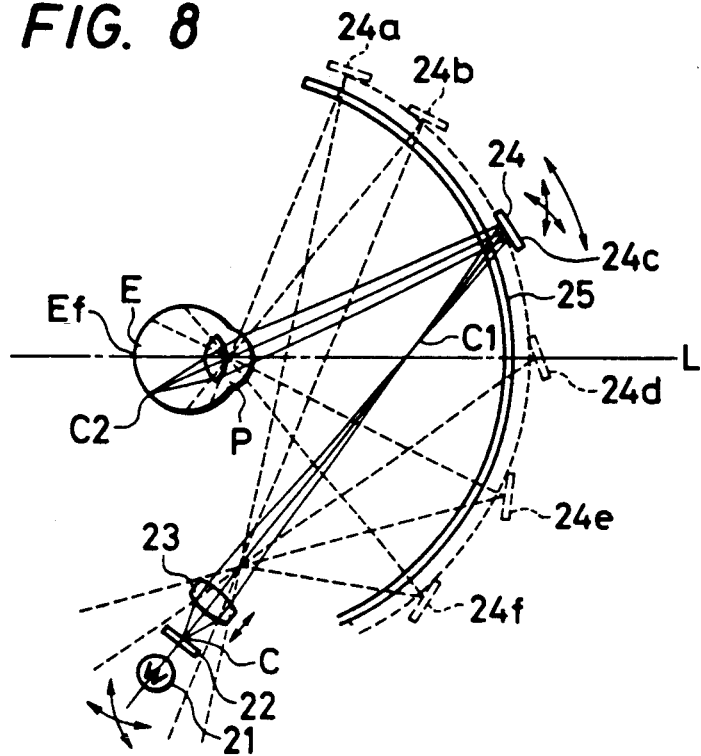
FIG. 8 is an illustration showing an optical arrangement according to another embodiment of the present invention.

FIG. 8 shows a perimeter according to another embodiment of the present invention. In this case, an index-projection imaging optical system is constituted by a light source 21, an index plate 22, and a focusing lens 23. A movable mirror 24 serves as a mirror reflection member. A semi-spherical non-diffusing barrier filter 25 which transmits part of the light emitted from the light source 21 is arranged between the movable mirror 24 and an eye E to be examined.

Referring to FIG. 8, light emitted from an index C on the index plate 22 illuminated with the light source 21 forms a spatial image C1 with the focusing lens 23, and is then transmitted through the barrier filter 25. The light beam is then reflected by the movable mirror 24 and enters the eye E again through the barrier filter 25, thus forming an index image C2 on a fundus Ef. A focusing position of the image C2 can vary depending on the diopter of the eye E upon movement in, or change in the refracting power of the focusing lens 23.

Figure 9:
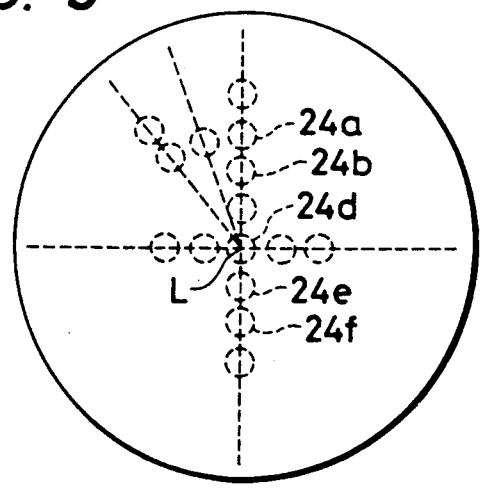
FIG. 9 is an illustration for explaining an operation of a movable mirror.

In order to change the position of the index image C2 on the fundus Ef of the eye E, the movable mirror 24 is moved three-dimensionally, as indicated by numerals 24a, 24b, 24c, . . . in FIG. 8, and the index-projection imaging optical system need only be rotated through a desired angle depending on the position of the mirror 24. In this case, in order to direct the index light beam toward the eye E, the movable mirror 24 must be inclined in synchronism with the optical system. FIG. 9 shows a state wherein the respective positions of the mirror 24 are observed from the side of the eye E. In practice, the mirror 24 changes its position continuously.

Figure 10:
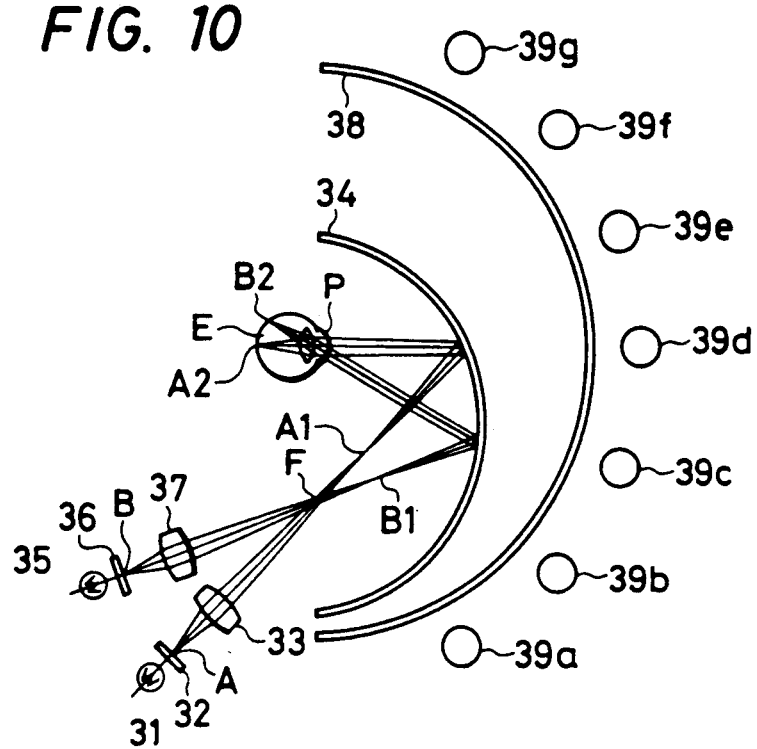
FIGS. 10 to 13 are illustrations showing optical arrangements according to another embodiment of the present invention.

FIG. 10 shows a perimeter according to still another embodiment of the present invention. A fixed-index-projection imaging optical system is constituted by a lower light source 31, an index plate 32 having an index A, and a focusing lens 33. An elliptical dome 34 is fixed as a mirror reflection member for guiding a light beam from the optical system into an eye E to be examined.

An index-projection imaging optical system is provided in addition to the fixed index-projection imaging optical system, and comprises a light source 35, an index plate 36 having an index B, and a focusing lens 37 so as to guide a light beam into the eye E through the dome 34.

Referring to FIG. 10, a light beam from the index A on the index plate 32 illuminated with the light source 31 temporarily forms a spatial image A1 by the focusing lens 33, and forms an index image A2 on a fundus Ef of the eye E through an iris P. A light beam from the index plate 36 illuminated with the light source 35 forms a spatial image B1 and then forms an index image B2 on the fundus Ef of the eye E through the iris P.

The focusing lenses 33 and 37 vary their refracting power or their positions depending on the diopter of the eye E, so as to always form a focal point on the eye E, thus correctly projecting the index images A2 and B2.

The position of the iris P of the eye E corresponds to a first focal point position of the dome 34. The light beams projected from the indexes A and B pass through a second focal point F of the dome 34, and can be freely scanned about the focal point F, thus varying the field angles at which the beams are projected into the eye E. A semi-spherical dome 38 arranged substantially about the iris P of the eye E is provided outside the dome 34, and light sources 39a, 39b, . . . , 39g are further arranged outside the dome 38. The dome 38 is formed of a light diffusing material, and the dome 34 is uniformly illuminated therethrough, by the light sources 39a, 39b, . . . 39g. Therefore, uniform illumination (i.e., background illumination) reaches the fundus Ef of the eye E through the dome 34.

In the above embodiment, the background illumination is made using the light diffusing surface of the dome 38. If the dome 34 is formed of the light diffusing material and a light source group is arranged therearound, the same effect can be provided.

Figure 11:
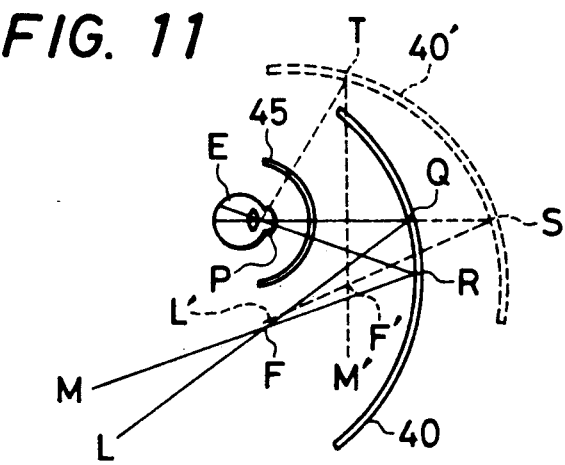

FIG. 11 shows fixed-index and index-projection imaging optical systems according to still another embodiment of the present invention. Optical axes L and M respectively indicate the fixed index-projection imaging optical system and index-projection imaging optical systems of FIG. 10. A light beam from fixed-index A propagates along the optical axis L, is reflected at a point Q on an elliptical dome 40, and is projected onto a fundus Ef of an eye E through an iris P. The index light beam propagates along the optical axis M, is reflected at a point R on the dome 40, and is then projected onto the fundus Ef, just as is the fixed-index image. The iris P of the eye E corresponds to a first focal point of the dome 40, and the fixed-index and index image beams pass through a second focal point F of the dome 40, just as in the embodiment of FIG. 10.

When the index is projected on a peripheral portion of the eye E, the dome 40 is rotated about the first focal point. An elliptical dome 40', indicated by broken lines in FIG. 11, illustrates the moved dome 40. In this case, the light beam from the fixed index A propagates along an optical axis L', is reflected at a point S on the dome 40', and reaches the eye E through a non-diffusing filter 45. On the other hand, the light beam from the index B propagates along an optical axis M', is reflected at a point T on the dome 40', and then reaches the eye E through the filter 45. Note that the filter 45 serves to conceal movement or contours of the dome 40.

Figure 12:
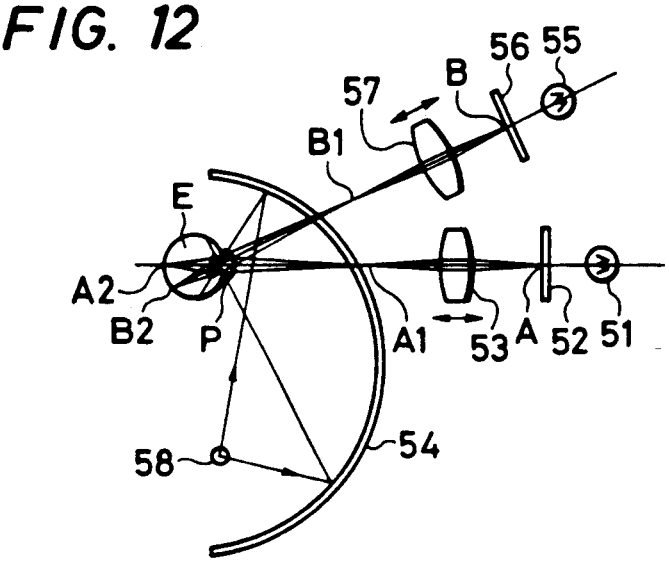

FIG. 12 shows a perimeter according to still another embodiment of the present invention. A fixed index-projection imaging optical system is constituted by a light source 51, a fixed index plate 52, and a focusing lens 53. A light-transmitting elliptical dome 54, using an iris P of an eye E as a first focal point, is fixed about the eye E. A light beam from an index A on the fixed index plate 52, illuminated with the light source 51, temporarily forms a spatial image A1 through the focusing lens 53, and then passes through the dome 54 to form a fixed index image A2 on a fundus Ef of the eye E through the iris P.

The focusing lens 53 changes its refracting power or its position depending on the diopter of the eye E, so as to always form a focal point on the eye E, thus correctly projecting the fixed index image A2. Since the optical system is rotatable about the iris P, an incident direction of the fixed index image A2 onto the fundus Ef can be changed as desired.

An index-projection imaging optical system is arranged in addition to the above optical system. An image based on an index B of an index plate 56 is guided into the eye E through a focusing lens 57 and the dome 54 so as to form an index image B2 on a fundus. The focusing lens 57 changes its refracting power or its position depending on the diopter of the eye E depending on the deopter of the eye E, just as does the focusing lens 53.

Furthermore, a background illumination light source 58 is arranged at a second focal point of the dome 54, so that the fundus Ef is illuminated with an image from the light source 58, which is formed on the iris P of the eye E through the dome 54.

Figure 13:
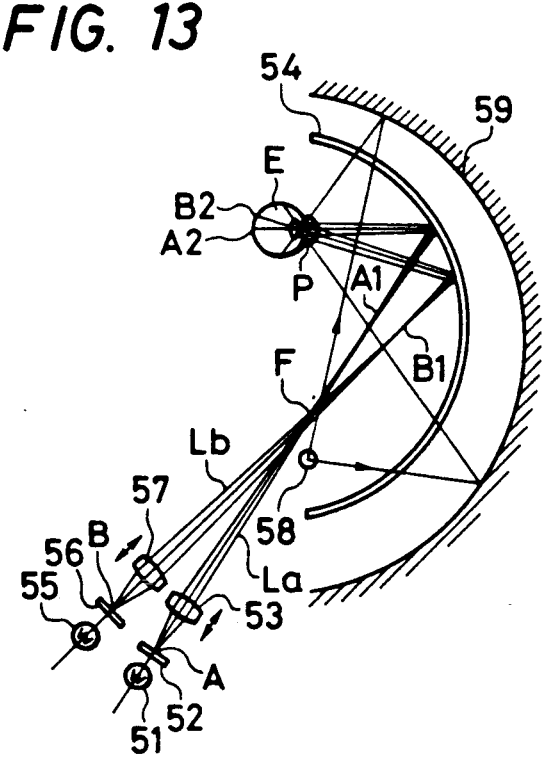

FIG. 13 shows a perimeter according to still another embodiment of the present invention. In this embodiment, an optical system comprises a fixed index-projection imaging optical system, an index-projection imaging optical system, a background illumination light source, and two elliptical domes. The fixed index-projection imaging optical system and the index-projection imaging optical system project fixed-index and index images onto a fundus of an eye E through an elliptical dome 54. A background illumination light source 58 illuminates the fundus through a reflective elliptical dome 59 arranged outside the dome 54. Light beams La and Lb emitted from both the optical systems pass through a second focal point F of the dome 54, and an iris P is at a first focal point of the domes 54 and 59. The light source 58 is arranged at a second focal point F of the dome 59. The light source can be a two-dimensional light source using lenses and the like.

A light beam from a fixed-index A of a fixed-index plate 52, illuminated with a light source 51, temporarily forms a spacial image A1 through a focusing lens 53, is reflected by the dome 54, and then forms an index image A2 on the fundus of the eye E through the iris P. Furthermore, a light beam from the light source 58 arranged at the second focal point F of the dome 59 is reflected by the dome 59, is transmitted through the dome 54, and is then focused on the iris P of the eye E, thus illuminating the fundus. In this case, the spacial images A1 and B1 have the same optical distance, and this distance is changed depending on the diopter of the eye E. The light beams La and Lb can be rotated three-dimensionally about the second focal point F of the dome 54, thus changing a field angle as desired.

A left-right eye switching operation will be described hereinafter.

Figure 14:
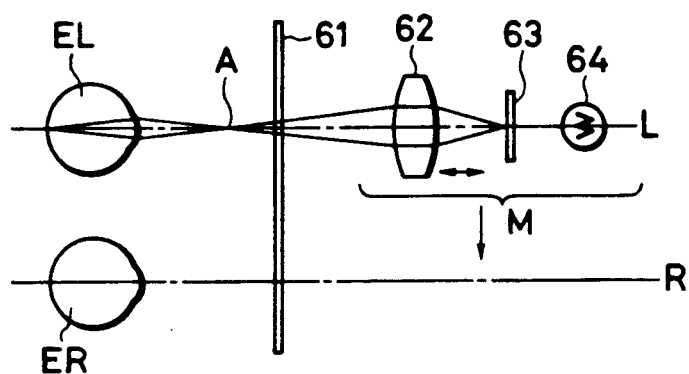
FIG. 14 is an illustration showing an optical arrangement for performing a left-right eye switching operation according to another embodiment of the present invention.

FIG. 14 shows a first embodiment of the left-right eye switching operation of the present invention, in which EL and ER indicate left and right eyes, respectively. A common semi-transparent plate 61 is placed in front of the eyes EL and ER, and an projection imaging optical system M including a focusing lens 62, an index 63, and an illumination light source 64 is arranged therebehind.

In FIG. 14, the optical axis of the optical system M coincides with a spatial axis L extending through the center of the iris of the left eye EL so as to allow examination of the eye EL. A light beam from the index 63 illuminated with an illumination light source 64 temporarily forms a spatial image A through the focusing lens 63 and the semi-transparent plate 61, and then enters the left eye EL, thus being focused on the fundus thereof. The optical axis of the optical system M is rotatable three-dimensionally about the iris of the left eye EL, and the focusing lens 62 is movable along the optical axis. The position of the lens 62 is determined depending on the refracting power of the eye EL.

In order to switch the eye to be examined from the left eye EL to the right eye ER, the optical system M of FIG. 14 need only be moved from the spatial axis L to a spatial axis R extending through the center of the iris of the right eye ER. The semi-transparent plate 61 conceals spatial movement of the optical system M from the eye to be examined.

Figure 15:
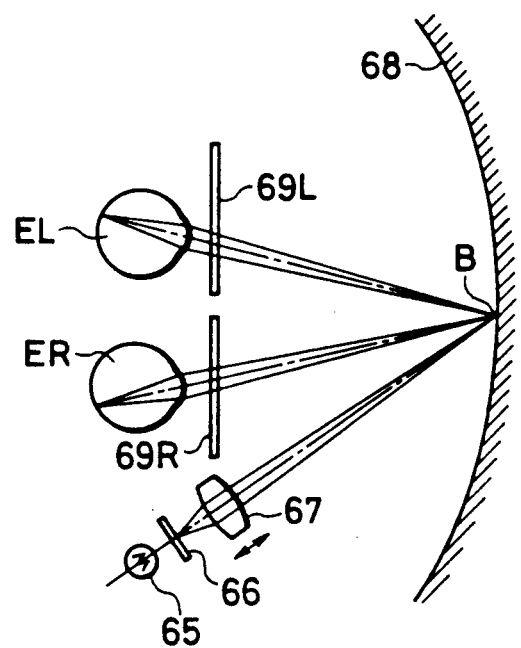
FIG. 15 is an illustration showing an optical arrangement according to another embodiment of the present invention.

FIG. 15 shows a second embodiment of the eye switching operation. In this case, an index 66 is illuminated with an illumination light source 65, and a light beam therefrom is focused on a semi-spherical dome 68 by the focusing lens 67 to form an index image B thereon, which is observed by a left or right eye EL or ER through a liquid crystal shutter 69L or 69R.

In this case, when light-shielding and light-transmitting states of the liquid crystal shutter 69L or 69R arranged in front of the eye EL or ER are selected separately, the left and right eyes EL and ER can be examined independently.

Figure 16:
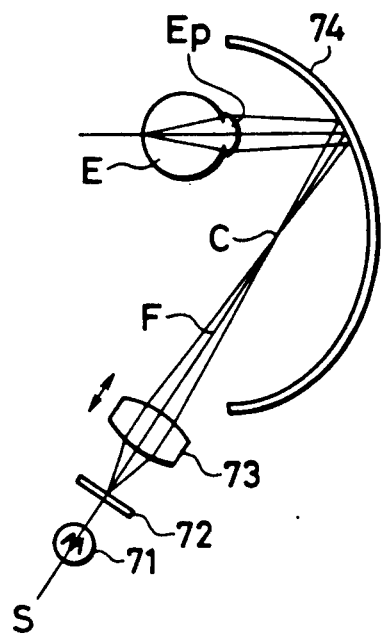
FIG. 16 is an illustration showing an optical arrangement according to another embodiment of the present invention.

FIG. 16 shows a third embodiment of the eye switching operation. In this embodiment, a light beam from an index 72 illuminated with an illumination light source 71 temporarily forms a spatial image C through a focusing lens 73, is reflected by an elliptical dome 74, and is then focused on a fundus through an iris Ep of an eye E.

The dome 74 is arranged so that a first focal point thereof corresponds to the iris Ep of the eye E, and an index projection light beam passes through a second focal point F of the dome 74. In order to change a position of the index image on the fundus of the eye E, an optical axis S of the optical system is rotated three-dimensionally about the second focal point F to adjust a field angle. In order to adjust the diopter of the eye E, the focusing lens 73 can be moved along the optical axis.

Figure 17:
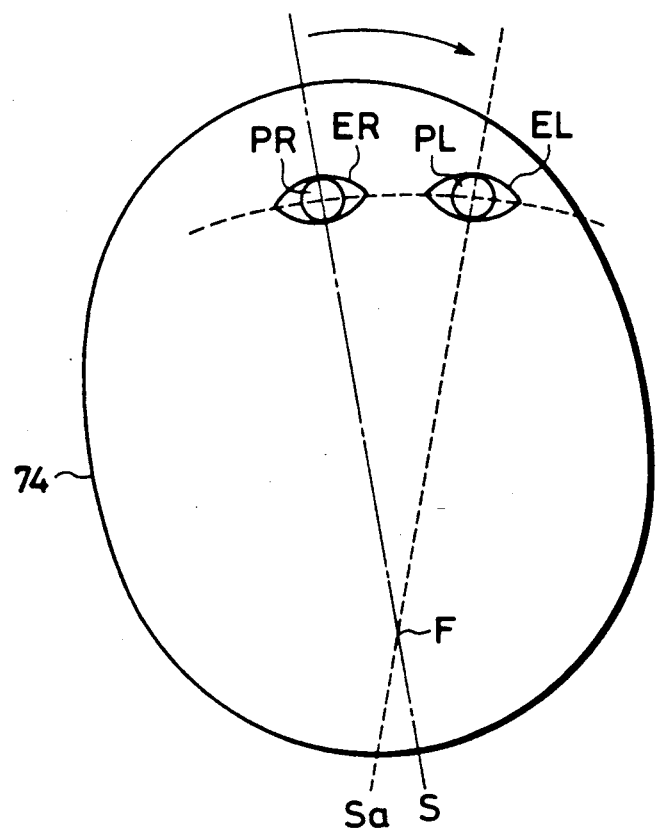
FIG. 17 is an illustration for explaining an operation of an elliptical dome in the arrangement shown in FIG. 16.

In this embodiment, in order to switch, e.g., from the right eye ER to the left eye EL, the dome 74 is moved as shown in FIG. 17, so that the first focal point thereof moves from an iris PR of the right eye to an iris PL of the left eye. The optical axis S of the optical system is then moved to a position as indicated by a broken line Sa, thus enabling perimetry of the left eye EL.

I claim:

1. A perimeter, comprising in the following order in an optical path:
   a semi-transparent member adapted to be disposed in a fixed position in front of an eye to be examined which transmits index light to the eye;
   an index imaging system behind said semi-transparent member in the optical path, said index imaging system having a predetermined index adapted to be projected onto a fundus of the eye to be examined by said index imaging system; and
   a light-shielding cover for shielding external light, wherein said index imaging system is in one body rotatable about the iris of the eye to be examined within a range of said semi-transparent member to displace a position of an index image on the fundus of the eye through said semi-transparent member, and said index imaging system comprises image forming means for moving an intermediate image of said index in the direction of the optical axis toward a position corresponding to a refractive power of the eye.

2. A perimeter according to claim 1, wherein said semi-transparent member has a semi-spherical surface with said eye being located at a center thereof.

3. A perimeter according to claim 1, wherein said semi-transparent member is a planar screen.

4. A perimeter according to claim 1, further comprising a fixed-index projection system.

5. A perimeter according to claim 4, wherein an index by said fixed-index projection system is arranged to be located at the same optical distance with respect to the examined eye as an index of said index projection system, and the spatial distances thereby from said eye are synchronously moved.

6. A perimeter according to claim 1, further comprising a background illumination system.

7. A perimeter according to claim 4, further comprising a background illumination system.

8. A perimeter according to claim 1, wherein index projection can be switched between a left eye and a right eye to be examined.

9. A perimeter according to claim 8, wherein said index projection system is movable in a direction perpendicular to the optical axis so as to switch between the left and right eyes.

10. A perimeter according to claim 1, wherein said semi-transparent member has an elliptical dome, whose first focal point is located at the iris of said eye, is arranged in front of said eye, and a background illumination source is arranged at a second focal point of said elliptical dome so as to project said index through said elliptical dome.

11. A perimeter according to claim 10, wherein a fixed-index projection system and said index projection system are arranged behind said elliptical dome.

12. A perimeter, comprising:
   a semi-transparent member adapted to be disposed in a fixed position in front of an eye to be examined which transmits index light to the eye;
   a mirror reflecting member adapted to be disposed behind said semi-transparent member in an optical path which reflects index light specularly to the eye;
   an index imaging system, said index imaging system having a predetermined index adapted to be projected onto a fundus of an eye to be examined by said index imaging system; and
   a light-shielding cover for shielding external light, wherein said index imaging system is in one body rotatable about the iris of the eye to be examined within a range of said semi-transparent member to displace a position of an index image on the fundus of the eye and wherein at least a part of said index imaging system is movable relative to the eye to be examined in the direction of the optical axis toward a position corresponding to a refractive power of the eye.

13. A perimeter according to claim 12, wherein said mirror reflection member is movable in three dimensions, and said index projection system is synchronized with movement of said mirror reflection member so that said index projection system projects the light beam from said index toward said eye.

14. A perimeter according to claim 12, wherein a plurality of said mirror reflection members are fixed in position, and said index projection system comprises means for directing a light beam toward each of said mirror reflection members.

15. A perimeter according to claim 12, wherein another mirror reflection member is arranged in a semi-spherical shape having said eye substantially at a center thereof.

16. A perimeter according to claim 12, wherein said mirror reflection member has an elliptical surface whose first focal point is located at an iris of said eye.

17. A perimeter according to claim 16, wherein a light-diffusing light source for background illumination is arranged behind said elliptical surface.

18. A perimeter according to claim 16, wherein said index is arranged at a second focal point.

19. A perimeter according to claim 16, wherein a background illumination source is arranged in front of said elliptical surface.

20. A perimeter according to claim 12, wherein said index projection system can be switched between a left eye and a right eye to be examined.

21. A perimeter according to claim 20, wherein light-shielding means which can select a light-shielding state and a light-transmitting state is arranged in front of the left and right eyes.

22. A perimeter according to claim 20, wherein a left-right eye switching operation is performed through an elliptical dome which has a first focal point at a predetermined position, and is rotatable about said predetermined position.

23. A perimeter comprising:
   a predetermined index to be projected onto a fundus of an eye to be examined;
   an index projection system which can form an intermediate image of said index in front of said eye, wherein said index projection system can be switched between a left eye and a right eye to be examined; and
   a mirror reflection member disposed in front of the eye to be examined in an optical path of said index projection system so as to keep a uniform field view, which specularly reflects index lights to the examined eye;
   wherein an optical system as being at least a part of said index projection system, is movable to displace a position of the index image on the fundus of said eye, and said index projection system comprises image forming means which moves said intermediate image in the direction of the optical axis and light-shielding means which can select a light-shielding state and a light-transmitting state is arranged in front of the left and right eyes and wherein said light-shielding means is a liquid crystal shutter.

24. A perimeter comprising:
   a predetermined index to be projected onto a fundus of an eye to be examined;
   an index projection system which can form an intermediate image of said index in front of said eye; and
   a mirror reflection member disposed in front of the eye to be examined in an optical path of said index projection system so as to keep a uniform field view, which specularly reflects index lights to the examined eye, wherein said mirror reflection member has an elliptical surface whose first focal point is located at an iris of said eye and wherein a second elliptical surface whose first focal point is located at the iris of said eye is arranged at the side of said elliptical surface opposing said eye;
   wherein an optical system as being at least a part of said index projection system, is movable to displace a position of the index image on the fundus of said eye, and said index projection system comprises image forming means which moves said intermediate image in the direction of the optical axis.

25. A perimeter wherein a predetermined index to be projected onto a fundus of an eye to be examined;
   an index projection system which can form an intermediate image of said index in front of said eye; and
   a mirror reflection member disposed in front of the eye to be examined in an optical path of said index projection system so as to keep a uniform field view, which specularly reflects index lights to the examined eye; wherein said mirror reflection member has an elliptical surface whose first focal point is located at an iris of said eye wherein a second elliptical surface whose first focal point is located at the iris of said eye is arranged at the side of said elliptical surface opposing said eye;
   wherein an optical system as being at least a part of said index projection system, is movable to displace a position of the index image on the fundus of said eye, and said index projection system comprises image forming means which moves said intermediate image in the direction of the optical axis, wherein a second elliptical surface whose first focal point is located at the iris of said eye is arranged at the side of said elliptical surface opposing said eye, wherein light beams from said index projection system and said fixed-index projection system pass through a second focal point of said second elliptical surface.

26. A perimeter comprising in the following order in an optical path:

a semi-transparent member adapted to be disposed in a fixed position in front of an eye to be examined which transmits index light to the eye;

a mirror reflecting member adapted to be disposed behind said semi-transparent member in the optical path which reflects index light specularly to the eye; and an index imaging system, said index imaging system having a predetermined index adapted to be projected onto a fundus of an eye to be examined by said index imaging system, wherein said index imaging system is in one body rotatable about the iris of the eye to be examined within a range of said semi-transparent member to displace a position of an index image on the fundus of the eye through said semi-transparent member and at least a part of said index imaging system is movable relative to the eye to be examined in the direction of the optical axis toward a position corresponding to a refractive power of the eye.

27. A perimeter comprising, in the following order in an optical path:

a semi-transparent member adapted to be disposed in a fixed position in front of an eye to be examined which transmits index light to the eye; and an index imaging system behind said semi-transparent member in the optical path, said index imaging system having a predetermined index adapted to be projected onto a fundus of the eye to be examined by said index imaging system, wherein said index imaging system is in one body rotatable about the iris of the eye to be examined within a range of said semi-transparent member to displace a position of an index image on the fundus of the eye through said semi-transparent member and at least a part of said index imaging system is movable relative to the eye to be examined in the direction of the optical axis toward a position corresponding to a refractive power of the eye.

28. A perimeter comprising in the following order in an optical path:

a semi-transparent member adapted to be disposed in a fixed position in front of an eye to be examined which transmits index light to the eye;

an index imaging system behind said semi-transparent member in the optical path, said index imaging system having a predetermined index adapted to be projected onto a fundus of the eye to be examined by said index imaging system; and a light-shielding cover for shielding external light, wherein said index imaging system is in one body three-dimensionally rotatable about the iris of the eye to be examined within a range of said semi-transparent member to displace a position of an index image on the fundus of the eye through said semi-transparent member and at least a part of said index imaging system is movable relative to the eye to be examined in the direction of the optical axis toward a position corresponding to a refractive power of the eye.

29. A perimeter, comprising:

an index mark projection system for projecting a target image to an eye to be examined along an optical axis of said index mark projection system, said index mark projection system generating a spatial image of an index mark between said index mark projection system and the eye to be examined, said index mark projection system having an adjusting member for generating the spatial image at a position corresponding to a refractive power of the eye;

a semi-transparent member optically disposed in a fixed position between said index mark projection system and the eye, said index mark being projected on the eye through said semi-transparent member; and means for three-dimensionally rotating said index mark projection system around an iris of the eye as a rotation center within a range of said semi-transparent member so as to project the image of said index mark from an arbitrary direction through said semi-transparent member to the eye along the optical axis of said index mark projection system.

30. A perimeter comprising:

an index mark projection system for projecting a target image to an eye to be examined, said index mark projection system generating a spatial image of an index mark between said index mark projection system and the eye to be examined, said index mark projection system having an adjusting member for generating the spatial image at a position corresponding to a refractive power of the eye;

a semi-transparent member optically disposed between said index mark projection system and the eye to be examined, said index mark being projected on the eye through said semi-transparent member;

mirror member disposed behind said semi-transparent member, said mirror means receiving the projection light from said index mark projection system through said semi-transparent member and reflecting said projection light through said semi-transparent member to the eye; and means for three-dimensionally and interlockingly rotating said index mark projection system and said mirror means around an iris of the eye as a rotation center so as to project the image of said index mark from an arbitrary direction to the eye.

31. A perimeter comprising:

an index mark projection system for projecting a target image to an eye to be examined along an optical axis of said index mark projection system, said index mark projection system generating a spatial image of an index mark between said index mark projection system and the eye to be examined, said index mark projection system having an adjusting member for generating the spatial image at a position corresponding to a refractive power of the eye;

a semi-transparent member adapted to be disposed in a fixed position in front of an eye to be examined which transmits index light to the eye;

a mirror reflecting member optically disposed between said index mark projection system and said semi-transparent member, said index mark image being reflected and projected to the eye by said mirror reflecting member; and means for three-dimensionally rotating the light flux of said index mark projection system around a point optically conjugate with an iris of the eye as a rotation center within a range of said index mark from an arbitrary direction through said semi-transparent member to the eye along the optical axis of said index mark projection system.

* * * * *

UNITED STATES PATENT AND TRADEMARK OFFICE
CERTIFICATE OF CORRECTION

PATENT NO. : 5,066,117

DATED : November 19, 1991

INVENTOR(S) : ISAO MATSUMURA

It is certified that error appears in the above-identified patent and that said Letters Patent is hereby corrected as shown below:

COLUMN 4

Line 23, "mirror 15a," should read -- mirrors 15a --.

COLUMN 6

Line 44, "depend-" should be deleted.
Line 45, "ing on the deopter of the eye E," should be deleted.

COLUMN 7

Line 5, "spacial" should read -- spatial --.
Line 12, "spacial" should read -- spatial --.
Line 24, "an projection" should read -- an index-projection --.

COLUMN 10

Line 22, "a mirror" should read -- ¶ a mirror --.
Line 39, change "wherein" to -- comprising --.

UNITED STATES PATENT AND TRADEMARK OFFICE
CERTIFICATE OF CORRECTION

PATENT NO. : 5,066,117
DATED : November 19, 1991
INVENTOR(S) : ISAO MATSUMURA

It is certified that error appears in the above-identified patent and that said Letters Patent is hereby corrected as shown below:

COLUMN 11

Line 1, "adapted'" should read -- adapted --.

COLUMN 12

Line 30, "mirror member" should read -- mirror means --.

Signed and Sealed this

Fifteenth Day of June, 1993

Attest:

MICHAEL K. KIRK

Attesting Officer

Acting Commissioner of Patents and Trademarks